(12) United States Patent
Chiu et al.

(10) Patent No.: US 10,835,759 B2
(45) Date of Patent: Nov. 17, 2020

(54) METHODS, APPARATUSES, AND SYSTEMS FOR CREATING A PATIENT-SPECIFIC SOFT BOLUS FOR RADIOTHERAPY TREATMENT

(71) Applicant: The Board of Regents of the University of Texas System, Austin, TX (US)

(72) Inventors: Tsuicheng D. Chiu, Plano, TX (US); Xuejun Gu, Dallas, TX (US); Jun Tan, Dallas, TX (US); Bo Zhao, Dallas, TX (US); Troy Long, Dallas, TX (US); Weiguo Lu, Dallas, TX (US); Tobin Strom, Dallas, TX (US); Kenneth Westover, Dallas, TX (US); Steve B. Jiang, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/488,134

(22) PCT Filed: Feb. 22, 2018

(86) PCT No.: PCT/US2018/019119
§ 371 (c)(1),
(2) Date: Aug. 22, 2019

(87) PCT Pub. No.: WO2018/156693
PCT Pub. Date: Aug. 30, 2018

(65) Prior Publication Data
US 2020/0001112 A1 Jan. 2, 2020

Related U.S. Application Data

(60) Provisional application No. 62/461,931, filed on Feb. 22, 2017.

(51) Int. Cl.
*A61N 5/10* (2006.01)
*B33Y 80/00* (2015.01)
(Continued)

(52) U.S. Cl.
CPC .... *A61N 5/1031* (2013.01); *A61N 2005/1087* (2013.01); *A61N 2005/1096* (2013.01);
(Continued)

(58) Field of Classification Search
CPC .................................................. A61N 5/1031
See application file for complete search history.

(56) References Cited

U.S. PATENT DOCUMENTS

| 2014/0249406 A1 | 9/2014 | Flynn et al. | |
| 2014/0277664 A1* | 9/2014 | Stump | G06F 30/00 700/98 |

(Continued)

OTHER PUBLICATIONS

Dubey, et al, "Innovative approach for generating soft silicon bolus using 3-dimensional printing for electron treatment of skin cancers in areas with irregular contours", International Journal of Radiation Oncology, 2016, pp. e606-e607 (Year: 2016).*

(Continued)

*Primary Examiner* — Edward Park
(74) *Attorney, Agent, or Firm* — Norton Rose Fulbright US LLP

(57) ABSTRACT

Methods, apparatuses, systems, and implementations for creating a patient-specific soft bolus for radiotherapy treatment are disclosed. 2D and/or 3D images of a desired radiotherapy treatment site may be acquired, such as the head, neck, skin, breast, anus, and/or vulva. A user may interact with one or more representations of the images via an interactive user interface such as a graphical user interface (GUI). The images may include target/avoidance structures and radiation beam arrangement. The user may interact with the images to create a visualization of a patient-specific (Continued)

bolus. The visualization and properties of the bolus may be modified as the user manipulates aspects of the image. Data corresponding to the bolus models may be used to create 3D printed negative molds of the bolus model using 3D printing technology. A soft patient-specific bolus may be cast using the 3D printed model.

30 Claims, 12 Drawing Sheets

(51) Int. Cl.
 *G16H 30/20* (2018.01)
 *B29C 33/38* (2006.01)
(52) U.S. Cl.
 CPC ........... *B29C 33/3842* (2013.01); *B33Y 80/00* (2014.12); *G16H 30/20* (2018.01)

(56) References Cited

U.S. PATENT DOCUMENTS

2016/0082289 A1* 3/2016 Frigo ................... A61N 5/1039
 600/1
2016/0256709 A1* 9/2016 Robar ................... A61N 5/1031

OTHER PUBLICATIONS

International Search Report and Written Opinion issued in counterpart International Patent Application No. PCT/US2018/019119, dated May 7, 2018.
Johnson, et al. "Innovative Approach for Generating Soft Silicone Bolus Using 3D Printing for Electron Treatment of Skin Cancers in Areas with Irregular Contours," *Cureus*, 2016, 8(9) (Poster).

* cited by examiner

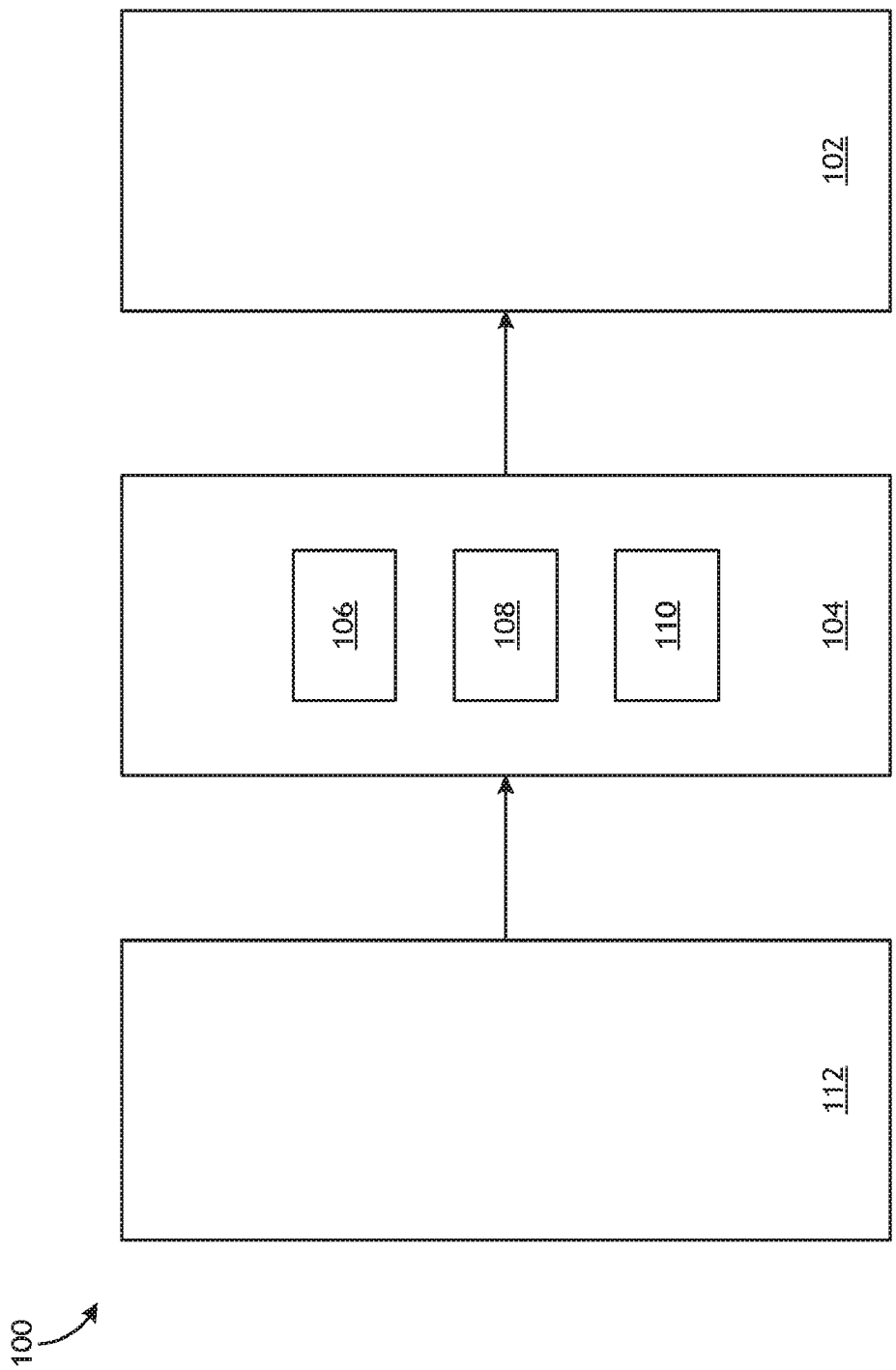

METHODS, APPARATUSES, AND SYSTEMS FOR CREATING A PATIENT-SPECIFIC SOFT BOLUS FOR RADIOTHERAPY TREATMENT

CROSS-REFERENCE TO RELATED APPLICATION

This application is a national phase under 35 U.S.C. § 371 of International Application No. PCT/US2018/019119, filed Feb. 22, 2019, which claims the benefit of priority to U.S. Provisional Patent Application No. 62/461,931, filed Feb. 22, 2017, the entire content of each of which are incorporated herein by reference in their entirety.

BACKGROUND

1. Field of the Invention

This disclosure relates generally to methods, apparatuses, and systems for creating a soft, patient-specific tissue compensator or bolus for use in radiotherapy treatment regimens.

2. Description of Related Art

Custom 3D boluses have been used in radiation therapy for various treatment sites to act as tissue compensators or to boost dose at shallow depth. Applications include various treatment sites such as the nose, ear, breast and more. Custom boluses are available from third party vendors. However, they are expensive and often must be fabricated off-site, introducing a time lag into standard radiation therapy planning workflows. Another common feature of currently available custom boluses is that they are composed of solid, hard plastic material and are therefore unable to conform to subtle changes in patient anatomy over the course of therapy. In addition, hard plastic is not acceptable when dealing with patients with painful open wounds as can often be seen in advanced cancer. For these reasons, construction of custom boluses out of a soft, pliable material has distinct advantages.

Non-custom soft boluses such as SuperFlab (Radiation Products Design, Inc. Albertville, Minn.) have a long history of being used as bolus material in radiation therapy. However, although these soft boluses have a soft texture, they are not moldable. Instead they consist of a layer of uniformly thick rubber that is applied to the patient surface. The material conforms to a patient's skin well in areas where the skin is relatively flat, such as on a patient's chest wall. However, in areas where the skin has an irregular surface, the soft bolus material lacks sufficient flexibility to conform to the patient's skin surface, leaving air gaps or resulting in day to day variations in setup. Furthermore, because SuperFlab is uniform in thickness, it cannot effectively produce intentional modulation of radiation dose distributions like a tissue compensator.

Recent advances in commercial 3D printing technology have facilitated in-house bolus manufacturing, which can greatly reduce the cost and turnaround of manufacturing boluses. A commercial 3D printer typically employs fused deposition modeling (FDM) technology. In this process, thin plastic filament is fed into and heated by an extruder where the nozzle dispenses liquid plastic at a programmed location. The liquid quickly deposits and quickly hardens to become rigid. This process builds a part layer by layer until completion. The disadvantages of using this process for making clinically used custom compensators are as follows: (1) they are composed of hard plastic which has large disadvantages for patient comfort or subtle day to day variability in anatomy; (2) the internal composition is heterogeneous because a bolus printed using FDM printing technology may have multiple unfillable spots depending upon the bolus shape and is prone to internal imperfections, resulting in undesirable air gaps that create problems from the standpoint of radiation dosimetry; and (3) 3D printing a completely solid piece not only requires long fabrication times tying up valuable resources but also reduces the life time of the printer dramatically. Therefore, it is desirable to achieve a process of fabricating a patient-specific soft bolus designed for radiation therapy using the high precision of 3D printing.

SUMMARY

As described above, boluses have been used as an accessory for radiation treatment for many years. Various types of boluses have been developed such as a commercially available universal bolus, a patient-specific moldable bolus, and a 3D printed patient-specific hard bolus. However, there is currently 1) no dosimetric-driven automatic or interactive bolus design process or, 2) no fabrication process for converting a bolus design to a soft bolus. Current commercial bolus design processes are trial-and-error based, which is not only time-consuming but may result in the end design failing to satisfy dosimetry requirements. This disclosure describes embodiments of an automatic or interactive patient-specific bolus design process that results in a patient-specific bolus design that is based directly from the end-dosimetry goal and is easy to satisfy user needs. These embodiments provide multiple advantages over current available bolus design processes and types. Compared to a non-patient specific bolus, a patient-specific bolus produced by the disclosed embodiments fits patient curvature and has higher dosimetric accuracy for wide-ranging clinical disease sites, including head and neck cancers, cutaneous cancers throughout the body, breast cancer, and anal and vulvar cancers. Compared to a patient-specific moldable bolus, a patient-specific bolus produced by the disclosed embodiments does not require molding onto the patient, which is sometimes not feasible or considerate of patient comfort for many anatomic locations such as the breast or surgical defects on the head and neck. An automatic or interactive bolus design process allows for rapid and accurate patient set-up prior to radiotherapy on a daily basis. Compared to a patient-specific hard bolus, a soft bolus is more comfortable than a hard bolus and allows for a better conformity between the bolus and the patient's skin. In the embodiments disclosed herein, a patient-specific soft bolus may be generated based on physician contoured structures and physician dosimetric prescription.

This disclosure includes embodiments of methods, apparatuses, and systems for creating a patient-specific soft bolus for use in radiotherapy treatment regimens. Some embodiments comprise a system that may include a computer system having at least one processor that may be configured to receive at least one patient-specific radiation treatment planning parameter. The at least one radiation treatment planning parameter include at least one image of a radiotherapy treatment area. The computer system may be further configured to enable an interaction between a user and the system. In some embodiments, the interaction may enable a modification of the at least one radiation treatment planning parameter. The computer system may be further configured to enable a creation of at least one 3D patient-specific bolus model based on at least one dosimetric requirement. The at least one 3D patient-specific bolus model may include a 3D representation of at least one patient-specific bolus for the radiotherapy treatment area. The computer system may be further configured to enable the sending of 3D representation data corresponding to the at least one 3D patient-specific bolus model. The 3D representation data may be configured to enable a creation of at least one physical 3D representation of the at least one patient-specific bolus. In some embodiments, the at least one radiation treatment planning parameter may include one or more of a computed tomography (CT) scan image, one or more of a target and avoidance structure, one or more dosimetric prescriptions for the one or more of the target and avoidance structure, and a radiation beam arrangement. In some embodiments, the computer system may be further configured to determine a type of beam treatment based on the at least one radiation treatment planning parameter, enable a creation of an initial 3D patient-specific bolus model based on the determined type of beam treatment, and enable a display of at least one radiation dose distribution on the initial 3D patient-specific bolus model. In some embodiments, the type of beam treatment may include one or more of photon beam treatment and electron beam treatment. In some embodiments, the at least one dosimetric requirement may be a user inputted dosimetric requirement. In some embodiments, the at least one radiation dose distribution may be configured to be interactively modified by the user. In some embodiments, enabling an interaction between the user and the system may include enabling the user to modify the at least one radiation dose distribution by performing one or more of morphing a dose distribution map and dragging the at least one radiation dose distribution to a different position, modifying a curvature of the at least one radiation dose distribution, and modifying a dimension of the at least one radiation dose distribution. In some embodiments, the computer system may be further configured to modify the at least one 3D patient-specific bolus model in real time to correspond to a user modification of the at least one radiation dose distribution.

In some embodiments, the computer system may be further configured to determine a type of beam treatment based on the at least one radiation treatment planning parameter, enable a creation of an initial 3D patient-specific bolus model based on the determined type of beam treatment, and enable an input of one or more of a physician dosimetric prescription on a target structure and at least one dosimetric constraint on an avoidance structure. In some embodiments, the type of beam treatment may include one or more of photon beam treatment and electron beam treatment. In some embodiments, the one or more of a physician dosimetric prescription on a target structure and at least one dosimetric constraint on an avoidance structure is configured to be interactively modified by the user. In some embodiments, the computer system may be further configured to modify the at least one 3D patient-specific bolus model in real time to correspond to a user modification of the one or more of a physician dosimetric prescription on a target structure and at least one dosimetric constraint on an avoidance structure. In some embodiments, enabling a creation of at least one physical 3D representation of the at least one patient-specific bolus may include creating a 3D printed mold of the at least one patient-specific bolus, the 3D printed mold comprising a negative shape of the at least one patient-specific bolus. In some embodiments, enabling a creation of at least one physical 3D representation of the at least one patient-specific bolus may further include casting the at least one patient-specific bolus using the 3D printed mold. In some embodiments, the at least one patient-specific bolus may include a soft and flexible material such as a silicone-based material.

Some embodiments of the present methods include a method of creating 3-dimensional (3D) representations of a bolus for radiotherapy treatment that may include receiving, by a computer system having at least one processor, at least one patient-specific radiation treatment planning parameter. In some embodiments, the at least one radiation treatment planning parameter includes at least one image of a radiotherapy treatment area. In some embodiments, the method may further include enabling, by the computer system, an interaction between a user and the system. In some embodiments, the interaction may enable a modification of the at least one radiation treatment planning parameter. In some embodiments, the method may further include enabling, by the computer system, a creation of at least one 3D patient-specific bolus model based on at least one dosimetric requirement. In some embodiments, the at least one 3D patient-specific bolus model may include a 3D representation of at least one patient-specific bolus for the radiotherapy treatment area. In some embodiments, the method may further include enabling, by the computer system, the sending of 3D representation data corresponding to the at least one 3D patient-specific bolus model. In some embodiments, the 3D representation data may be configured to enable a creation of at least one physical 3D representation of the at least one patient-specific bolus. In some embodiments, the at least one radiation treatment planning parameter may include one or more of a computed tomography (CT) scan image, one or more of a target and avoidance structure, and a radiation beam arrangement. In some embodiments, the method may further include determining, by the computer system, a type of beam treatment based on the at least one radiation treatment planning parameter, enabling, by the computer system, a creation of an initial 3D patient-specific bolus model based on the determined type of beam treatment; and enabling, by the computer system, a display of at least one radiation dose distribution on the initial 3D patient-specific bolus model. In some embodiments, the type of beam treatment may include one or more of photon beam treatment and electron beam treatment. In some embodiments, the at least one dosimetric requirement may be a user inputted dosimetric requirement. In some embodiments, the one or more radiation dose distribution may be configured to be interactively modified by the user. In some embodiments, the method may further include enabling an interaction between the user and the system enabling the user to modify the at least one radiation dose distribution by performing one or more of morphing a dose distribution map and dragging the at least one radiation dose distribution to a different position, modifying a curvature of the at least one radiation dose distribution, and modifying a dimension of the at least one radiation dose distribution. In some embodiments, the method may further include modifying, by the computer system, the at least one 3D patient-specific bolus model in real time to correspond to a user modification of the at least one radiation dose distribution.

In some embodiments, the method may further include determining, by the computer system, a type of beam treatment based on the at least one radiation treatment planning parameter; enabling, by the computer system, a creation of an initial 3D patient-specific bolus model based on the determined type of beam treatment; and enabling, by the computer system, an input of one or more of a physician dosimetric prescription on a target structure and at least one dosimetric constraint on an avoidance structure. In some embodiments, the type of beam treatment may include one or more of photon beam treatment and electron beam treatment. In some embodiments, the one or more of a physician dosimetric prescription on a target structure and at least one dosimetric constraint on an avoidance structure may be configured to be interactively modified by the user. In some embodiments, the method may further include modifying, by the computer system, the at least one 3D patient-specific bolus model in real time to correspond to a user modification of the one or more of a physician dosimetric prescription on a target structure and at least one dosimetric constraint on an avoidance structure. In some embodiments, enabling a creation of at least one physical 3D representation of the at least one patient-specific bolus may include creating a 3D printed mold of the at least one patient-specific bolus. In some embodiments, the 3D printed mold may include a negative shape of the at least one patient-specific bolus. In some embodiments, enabling a creation of at least one physical 3D representation of the at least one patient-specific bolus may further include casting the at least one patient-specific bolus using the 3D printed mold. In some embodiments, the at least one patient-specific bolus may include a soft and flexible material such as a silicone-based material.

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, or a component of a system, that "comprises," "has," "includes" or "contains" one or more elements or features possesses those one or more elements or features, but is not limited to possessing only those elements or features. Likewise, a method that "comprises," "has," "includes" or "contains" one or more steps possesses those one or more steps, but is not limited to possessing only those one or more steps. Additionally, terms such as "first" and "second" are used only to differentiate structures or features, and not to limit the different structures or features to a particular order.

Any embodiment of any of the disclosed methods, systems, system components, or method steps can consist of or consist essentially of—rather than comprise/include/contain/have—any of the described elements, steps, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

BRIEF DESCRIPTION OF THE DRAWINGS

The following drawings illustrate by way of example and not limitation. For the sake of brevity and clarity, every feature of a given method or system is not always labeled in every figure related to that method or system. Identical reference numbers do not necessarily indicate an identical feature. Rather, the same reference number may be used to indicate a similar feature or a feature with similar functionality, as may non-identical reference numbers.

FIG. 1 depicts an exemplary 3D imaging and patient-specific bolus design system according to an embodiment of the disclosure.

DETAILED DESCRIPTION OF ILLUSTRATIVE EMBODIMENTS

Figures 2A, 2B:
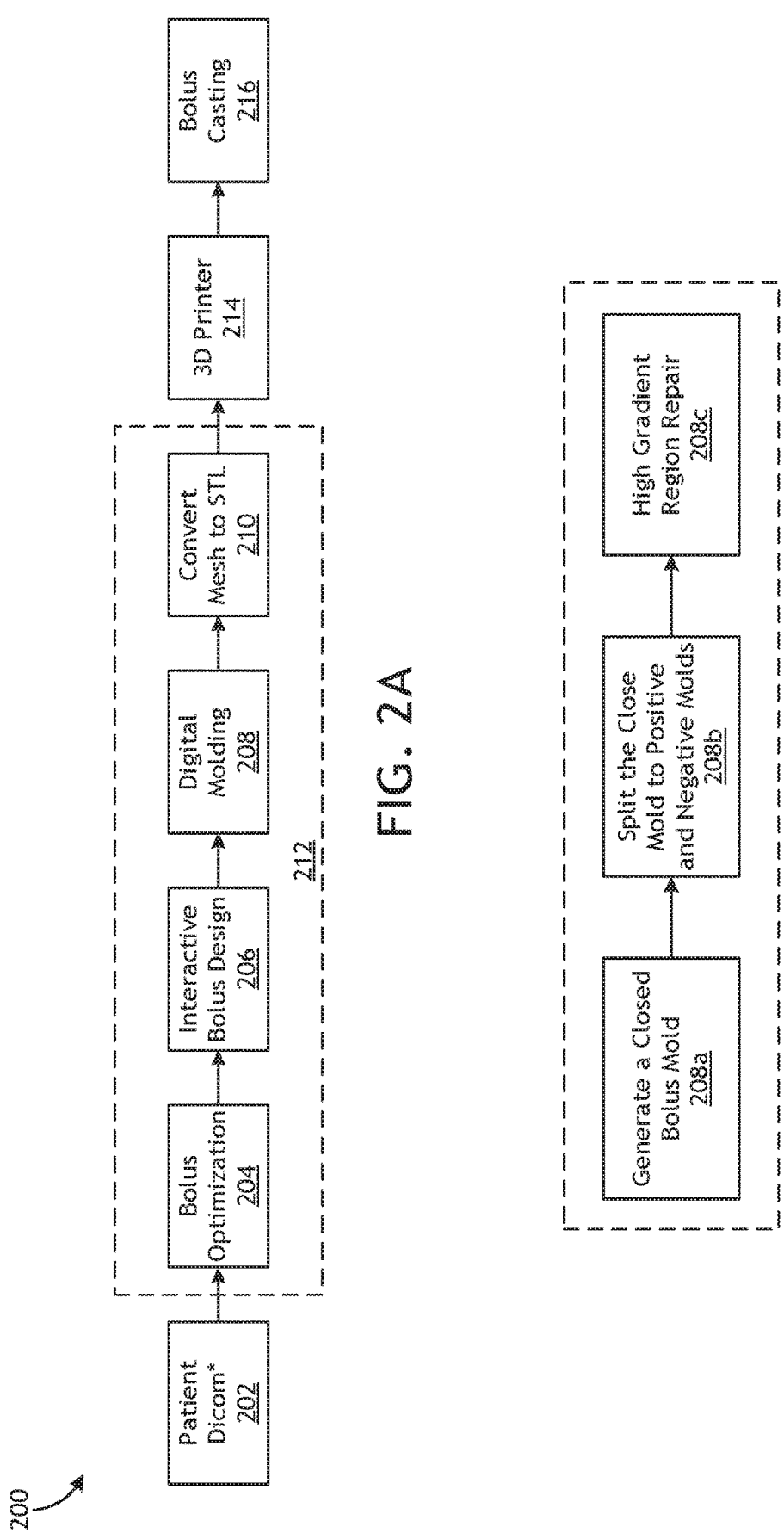
FIGS. 2A-B depict an exemplary method for creating 3D representations of a patient-specific bolus according to an embodiment of the disclosure.

Tissue-equivalent boluses are often used in high-energy radiation therapy to compensate for surface irregularities on patients and to enhance radiation doses to the skin. Currently available boluses often consist of universal sheet-based gel polymer materials and are not ideal for many common clinical scenarios where the treated surface of a patient is irregular such as the head and neck, breast, fingers and toes, anus, and vulva. Recent developments in 3D printing technology provide solutions for designing patient-specific boluses. However, currently available methods for patient-specific bolus fabrication are cumbersome. The bolus design procedure is frequently a trial-and-error process, which is inefficient and a waste of clinical resources. Additionally, currently available manufactured boluses consist of a hard plastic material that is unacceptable to most patients because of discomfort. Hard plastic placed on existing tumor-associated or radiation-developed wounds can be extremely painful and difficult to tolerate for the patient.

This disclosure presents embodiments of an automatic and interactive bolus design processing interface that implements several processes for fabrication of dosimetric-driven patient-comfort-oriented soft boluses. The design platform may provide an easy solution for bolus design that results in a soft bolus that is far more tolerable for patients than other currently available solutions. In this way, the disclosed embodiments enable 1) automatic and interactive bolus design based on physician contoured structures and physician dosimetric prescription and 2) conversion of the bolus design to a physical soft bolus. Referring now to the drawings, FIG. 1 depicts an exemplary 3D imaging and patient-specific bolus design system 100 according to an embodiment of the disclosure. In the embodiment shown, an imaging device 102 may be provided. The imaging device 102 may be a CT scanning device or other suitable device capable of providing 2D and/or 3D imaging capabilities. A processing device 104 may be capable of receiving the images taken by the imaging device. Processing device 104 may be a part of a computer system that may include standard components such as a hard drive, monitor, printer, keyboard, and mouse, among others, that may enable a user to interact with the processing device 104. In the embodiment shown, processing device 104 may include one or more of an automatic and interactive bolus design application 106, a 3D imaging application 108, and a radiation treatment planning system (TPS) application 110. In some embodiments, interactive bolus design application 106 may be configured to receive one or more CT images from imaging device 102. In some embodiments, TPS application 110 may be configured to receive one or more CT images from imaging device 102 and modify the one or more images with radiation treatment information such as target/avoidance structures, radiation beam arrangements, and a radiation dose distribution such as radiation dose map and/or radiation iso-dose lines. In these embodiments, automatic and interactive bolus design application 106 may be configured to receive the one or more modified images from TPS application 110. In some embodiments, automatic and interactive bolus design application 106 may segment the one or more images into one or more regions and enable a selection of one or more regions. In some embodiments, the one or more regions may correspond to the radiation treatment information provided by TPS application 110. In some embodiments, the selection of the one or more regions may be done automatically by processing device 104. In some embodiments, the selection of the one or more regions may be done by a user. In some embodiments, the user may interact with the one or more regions to modify the radiation treatment information to correspond to a desired radiation treatment plan.

In some embodiments, 3D image application 108 may generate one or more 3D images of a bolus model. In some embodiments, the bolus model corresponds to a bolus for implementing the desired radiation treatment plan of the user. In some embodiments, the one or more 3D images may be converted to stereolithography (.stl) format and/or displayed as 3D orthographic images to enable orthographic views of the bolus model. The one or more 3D images may be displayed to a user and 3D image application 108 may enable a user to view and manipulate the one or more 3D images. In some embodiments, image manipulation capabilities may include capabilities to rotate, zoom, mark, color, and select the one or more images. In the embodiment shown, processing device 104 may be configured to send data corresponding to the one or more 3D images to a 3D printing device 112. 3D printing device 112 may create one or more 3D physical representations of the received one or more 3D images. In some embodiments, the one or more 3D physical representations may be a positive bolus mold and/or a negative bolus mold.

FIGS. 2A-B depict an exemplary method 200 for creating 3D representations of a patient-specific bolus according to an embodiment of the disclosure. In some embodiments, a method for creating a patient-specific soft bolus may include three stages: 1) designing, 2) molding, and 3) casting. In some embodiments of the designing stage, one or more CT images, target/avoidance structures, RT plan information, and a pre-calculated 3D dose (with or without initial bolus structure) are input into an interactive bolus design application implemented by one or more processing devices. In some embodiments, physicians can make a dose prescription based on tumor structure and constraints on dose limiting structures and an automatic optimization interface can generate a bolus shape to meet the dosimetric requirements. In some embodiments, the dose distribution is superimposed on CT images as radiation iso-dose lines. In some embodiments, when a user modifies or drags the iso-dose lines, a corresponding bolus shape is changed simultaneously with the aid of real-time electron beam range optimization and dose calculation. Once the desired dose distribution is achieved, the designed 3D bolus shape can be used to digitally create positive and negative molds in .STL file format for 3D printing. In some embodiments, the two printed molds are used to cast a soft bolus with certified skin safe silicone rubber.

In one embodiment of the disclosure, method 200 may be implemented by system 100. In the embodiment shown in FIG. 2, method 200 may begin at step 202 with structure preparing of a patient DICOM (Digital Imaging and Communication in Medicine) file. In some embodiments, structure preparing is a step where physicians design a desired and proper bolus and dosimetrists finish contouring the organs. This structure preparing step may be suitable for any treatment planning system that creates the structure contours by defining an outline as discrete points on each CT image slice in DICOM format. In some embodiments, 1 mm CT simulation slice thickness is the favorite to create smooth and accurate boluses; however, both 1 mm and 3 mm can be used to fabricate the boluses. The thinner the slice thickness is, the higher the accuracy of interpolations between CT slices can be. The patient DICOM prepared in step 202 may include planning CT images, treatment volumes and critical organs delineated by clinicians, and/or treatment plans (including, e.g., radiation beams orientation and radiation dose).

Method 200 may continue with bolus molding steps 204, 206, 208, 210. In some embodiments, the bolus is molded digitally. In some embodiments, the DICOM structure created in step 202 is exported and loaded into a bolus design interface 212. In some embodiments, the automatic/interactive bolus design interface may be a graphical user interface (GUI). In some embodiments, the automatic/interactive bolus design interface may be automatic and interactive bolus design application 106. In some embodiments, the automatic/interactive bolus design interface can be coded in MATLAB (Mathworks, USA). In step 204, the automatic/interactive bolus design interface may display one or more CT images from the patient DICOM along with treatment information such as radiation dose distribution map and/or radiation iso-dose lines. Based on the patient DICOM data, a bolus optimized to implement the treatment plan is automatically created. In step 206, a user may interact with the images in the interactive bolus design interface to modify the bolus design. In some embodiments, the user may modify the bolus shape by modifying or dragging one or more radiation iso-dose lines. In some embodiments, the user may modify the bolus shape by morphing radiation dose distribution.

In step 208, the automatic/interactive bolus design interface may take 2D discrete structure points from each slice of the image to create a raw 3D bolus mesh model. One or more smoothing algorithms or functions may be applied to the raw 3D bolus mesh model to create a smooth and more continuous model. In some embodiments, step 208 may comprise substeps 208a, 208b, and 208c. In step 208a, a closed bolus mold may be generated based on the smoothed 3D bolus mesh model. In step 208b, the closed bolus mold may be split into a positive mold and a negative mold and, in step 208c, the molds may be subjected to high gradient region repair. In some embodiments, 2 mm thick positive and negative mesh molds are created by digitally molding the smoothed 3D bolus model. In step 210, the smoothed 3D bolus model may be converted to .STL file format.

Method 200 may continue with bolus casting steps 214 and 216. In conventional system, the .STL file is usually sent to the 3D printer to fabricate the bolus directly. However, in some embodiments of the present method, the 3D printer is not used to fabricate the final product directly but is instead used to create accurate bolus molds that can then be used to cast silicone boluses. Exemplary 3D printers that can be used for implementing the present embodiments include the Makerbot Z18 and Makerbot Replicator Plus. Exemplary printing settings can be 3% filling, 0.3 mm layer height with bridges and supports as needed. Both of these exemplary printers have 11 micron positioning precision in X and Y (printing plate plane) directions and 2.5 micron in Z (elevational) direction. However, other suitable 3D printers and/or printing settings may be used.

In step 214, the 3D printer receives the .STL file of the smoothed 3D bolus model and prints the positive and/or negative molds of the bolus. In step 216, the 3D printed molds may be used to cast a patient-specific soft bolus. In some embodiments, a silicone material is used such as Smooth-on Ecoflex 00-30 (Smooth-on Inc., Macungie, Pa.) but other suitable silicone materials or other soft materials may be used. Cured silicone is a certified skin safe material that can minimize skin irritation and sensitization. Cured silicone is also very soft, very strong and very pliable. It may be stretched many times to its original size without tearing and can rebound to its original form without distortion. This silicone may be created using two parts of liquid compounds. After mixing up, the pot life may be about 45 minutes and may be cured in 4 hours. The curing process could be accelerated by adding a silicone cure accelerator to create the product in about 1.5 hours. Degassing the silicone liquid is important to achieve a high uniformity in the final product without air bubbles.

In some embodiments, after the positive and negative molds are printed and cleaned up, these two pieces are assembled together by using a hot glue gun to seal any possible leaking area. The degassed mixed silicone liquid is poured into the assembled mold. In some embodiments, a casting box may be used to support the molds during the casting process. Once the silicone is cured and hardens, the final product can be easily demolded and is ready for use. Depending upon the size (volume and surface area) and complexity, the process time may be varied.

Figure 3A:
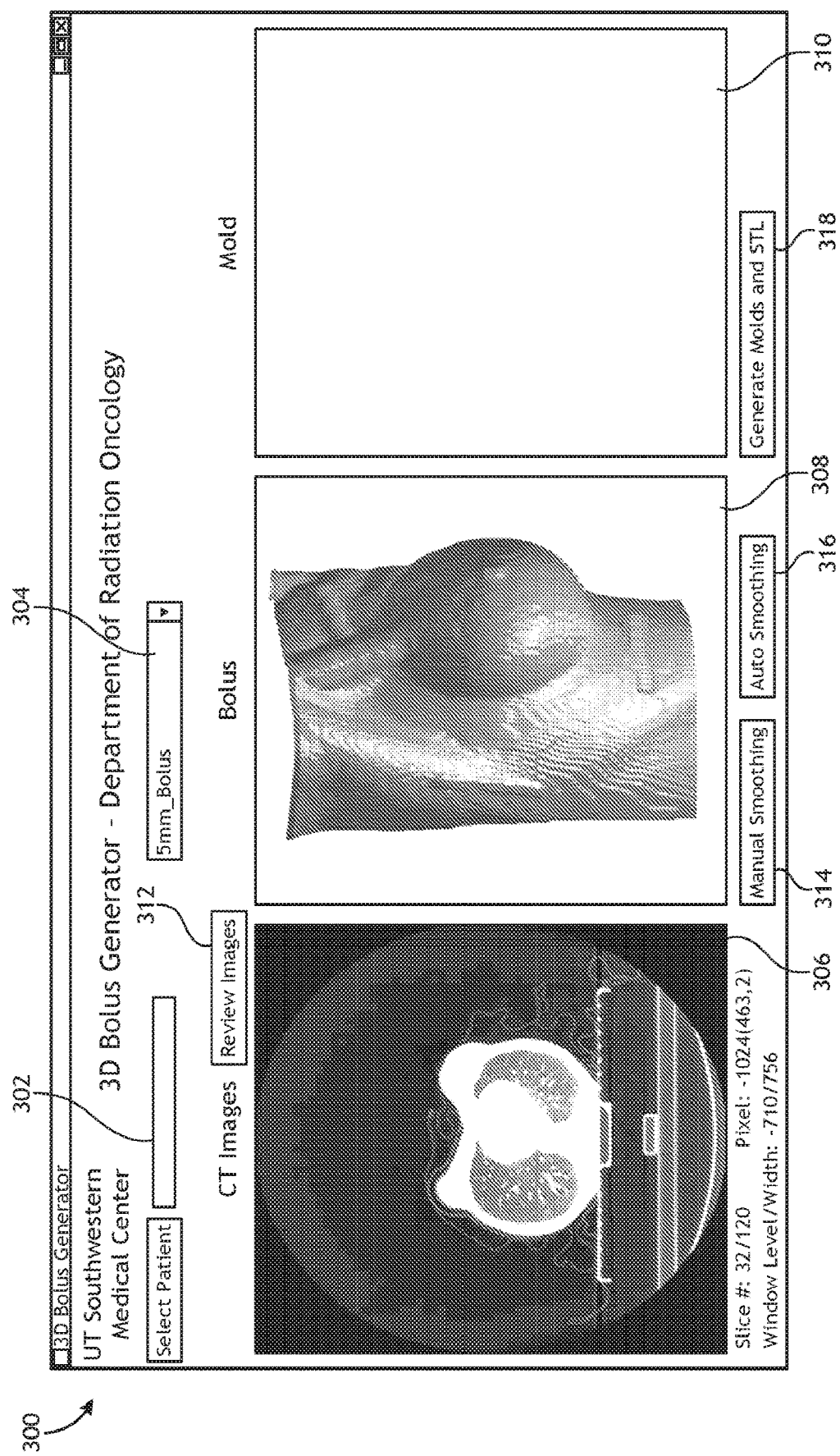
FIGS. 3A-B depict an exemplary interactive graphical user interface (GUI) according to an embodiment of the disclosure.
Figure 3B:
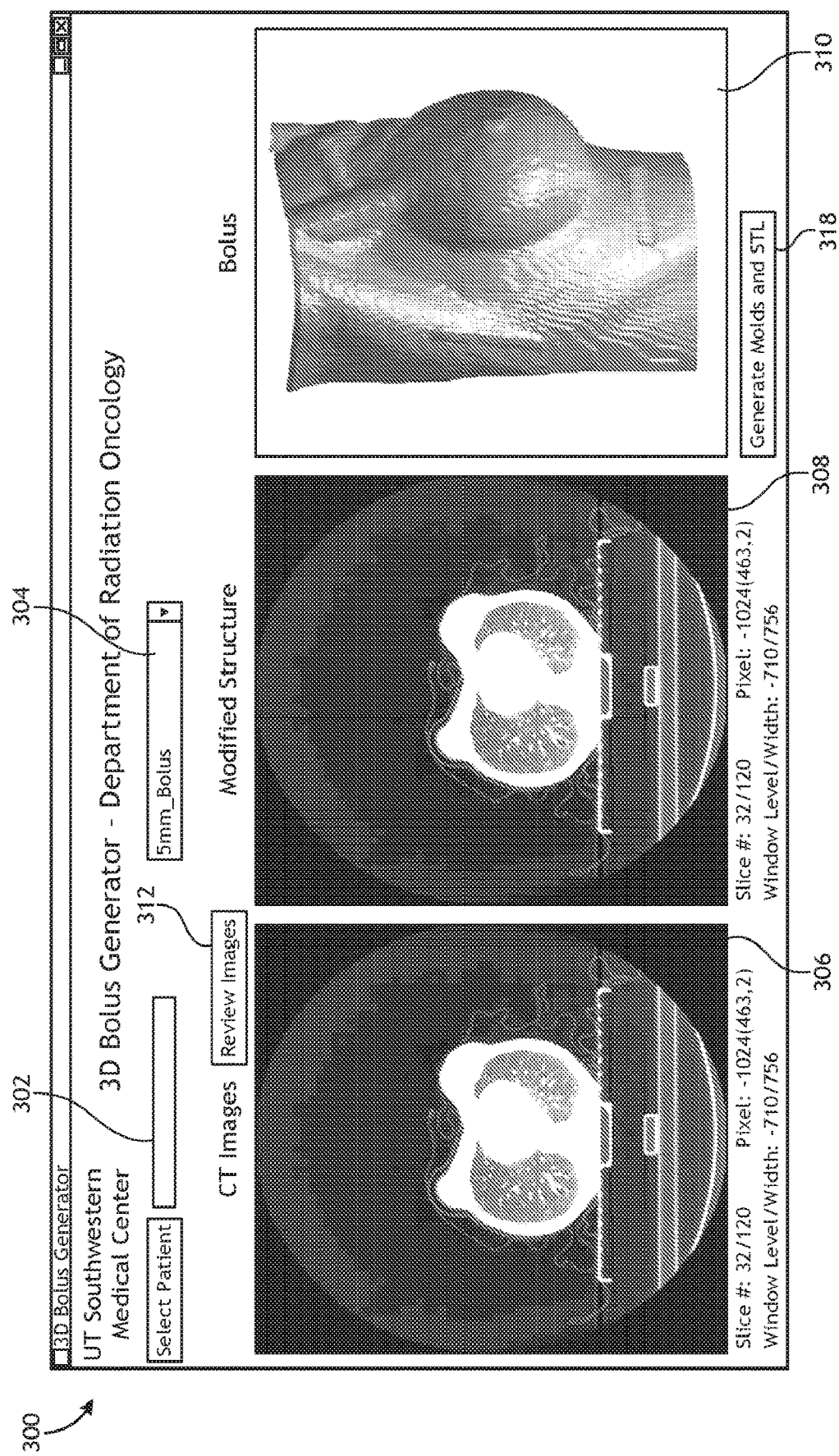

FIGS. 3A-B depict an exemplary interactive graphical user interface (GUI) 300 according to an embodiment of the disclosure. In some embodiments, GUI 300 may include a patient selection field 302, a bolus thickness field 304, and image fields 306, 308, 310. In some embodiments, various option icons may be provided such as one or more review option icons 312, one or more smoothing option icons 314, 316, and one or more mold generation option icons 318. In the embodiments shown in FIGS. 3A-B, a user may select a particular patient from the patient selection field 302 and may select a desired bolus thickness from the bolus thickness field 304. In some embodiments, the user can select a patient by browsing though one or more folders, typing in a patient's name, or selecting a designated patient from a drop down menu list. In some embodiments, the user can select a desired bolus thickness using methods similar to selecting the patient. In the embodiments shown, image field 306 may display one or more CT images from the selected patients DICOM file. In some embodiments, the user may be able to scroll through different slices of the CT image and zoom in and out of the image. In the embodiment shown in FIG. 3A, image field 308 may display a 3D bolus mesh model of the CT image shown in image field 306. The user may smooth the 3D bolus mesh model by selecting a manual smoothing option 314 and/or an automatic smoothing option 316. In some embodiments, the user can interact with the 3D bolus mesh model to select certain meshes on the model for smoothing. The user may also be able to have zooming and rotation functionality for the 3D bolus mesh model. In some embodiments, a 3D model of one or more molds (e.g., positive and/or negative molds) corresponding to the 3D bolus mesh model may be displayed in image field 310. The user may instruct a 3D printer to generate the bolus molds by selecting mold generation option icon 318. Up selection of the mold generation option icon 318, a .STL file of the bolus molds is created and sent to the 3D printer. In the embodiment shown in FIG. 3B, image field 308 may display a modified CT image that is different from the CT image shown in image field 306. As the CT image displayed in image field 308 is modified automatically by the system or manually by the user, image field 310 may display a 3D bolus mesh model of the modified CT image.

Figure 4A:
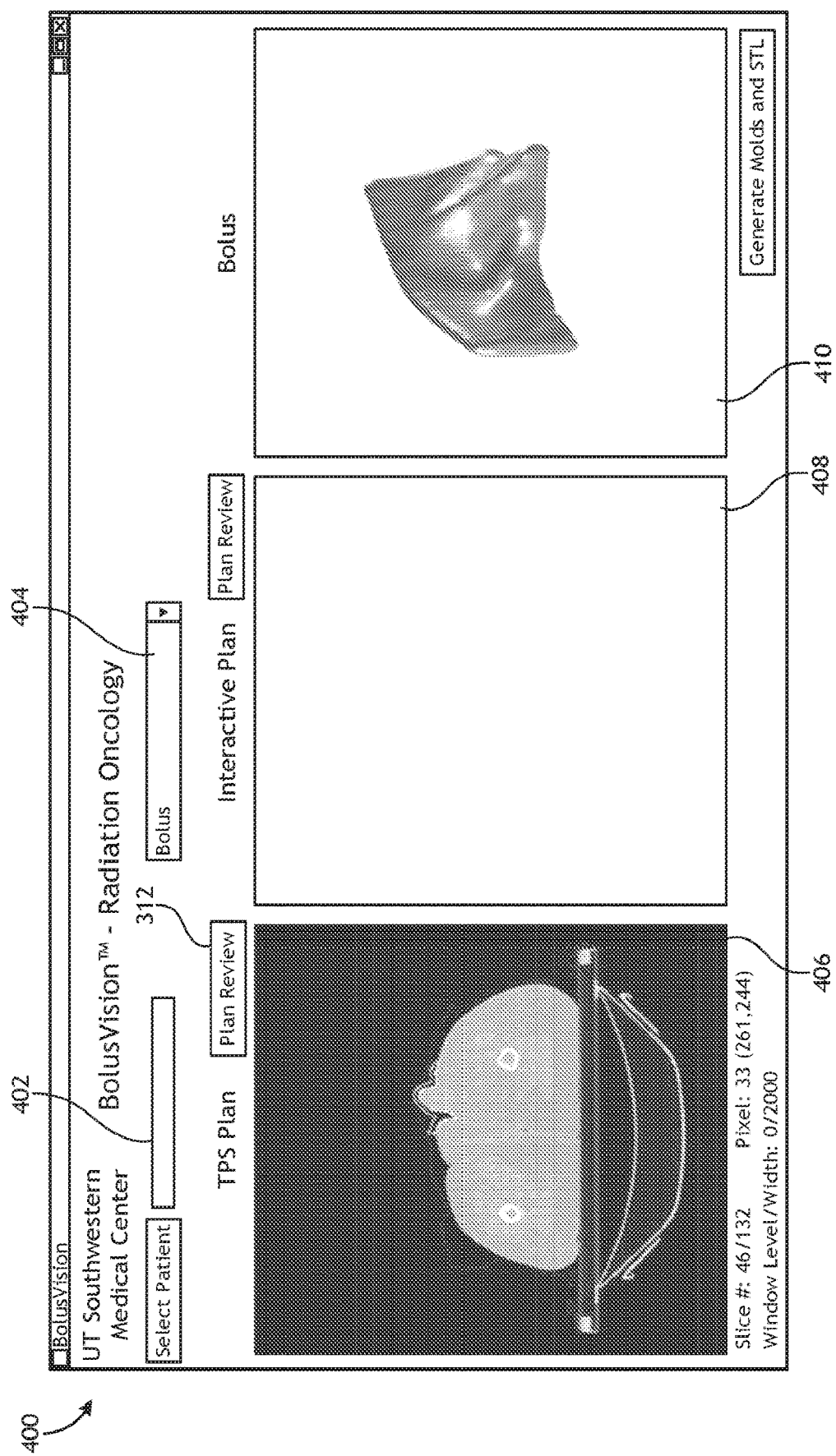
FIGS. 4A-B depict an exemplary interactive graphical user interface (GUI) according to another embodiment of the disclosure.
Figure 4B:
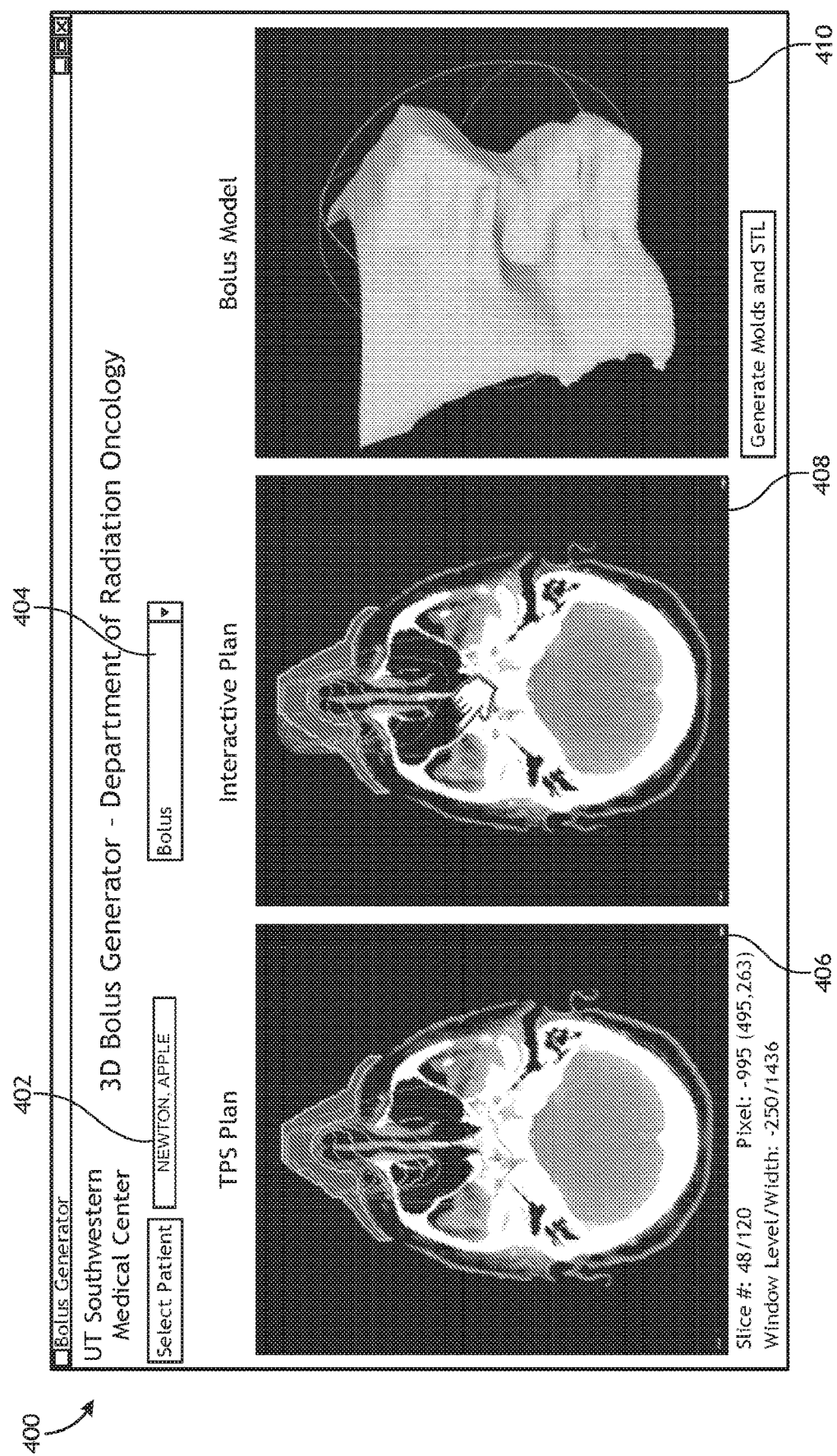

FIGS. 4A-B depict an exemplary interactive graphical user interface (GUI) 400 according to another embodiment of the disclosure. In the embodiments shown in FIGS. 4A-B, patient selection field 402 and a bolus thickness field 404 enable functionality similar to the embodiments discussed previously. The interactive bolus design interface can communicate with a radiation TPS (e.g., Pinnacle, Philips Healthcare) which can send treatment planning information, such as simulation CT images, target/avoidance structures, and radiation beam arrangements to the interface. In the embodiments shown in FIGS. 4A-B, image field 406 displays a TPS plan image that may include a CT image with target/avoidance structures and radiation beam arrangements. This image may show an initial bolus and resulting radiation dose distribution. In the embodiments shown, image field 408 displays an interactive plan image that enables the user to modify the TPS plan image. In some embodiments, the user may modify the radiation dose distribution such as by morphing the radiation dose distribution map. In some embodiments, the user may modify the radiation dose distribution such as by modifying one or more of the radiation iso-dose lines. In the embodiments shown, image field 410 may display a 3D bolus mesh model of a bolus that would be effective for implementing the treatment plan denoted by the radiation dose distribution of the image displayed in image field 408. In some embodiments, the 3D bolus mesh model may be created automatically. In some embodiments, the 3D bolus mesh model may be modified in real time as the user modifies the image in image field 408. The user may smooth the 3D bolus mesh model image and generate molds of the bolus with functionality similar to the embodiments discussed previously.

In some embodiments, the interface may include two different bolus design modules: one for photon-beam treatment and one for electron-beam treatment. For photon-beam treatment, it is often a requirement that the bolus have a uniform, defined thickness. In this case, the bolus structure can be derived from the radiation target structure and beam arrangement of the TPS plan. The interface may automatically create a uniform bolus in the plane of the incident beams. For electron-beam treatment, a non-uniform bolus is used to modulate beams to achieve a desired radiation dose distribution. The interface may allow users to manually morph radiation dose distribution map and/or drag radiation iso-dose lines according to preference. In response, the interface may automatically revises the shape of the 3D bolus model shown in image field 410 accordingly.

Figure 5B:
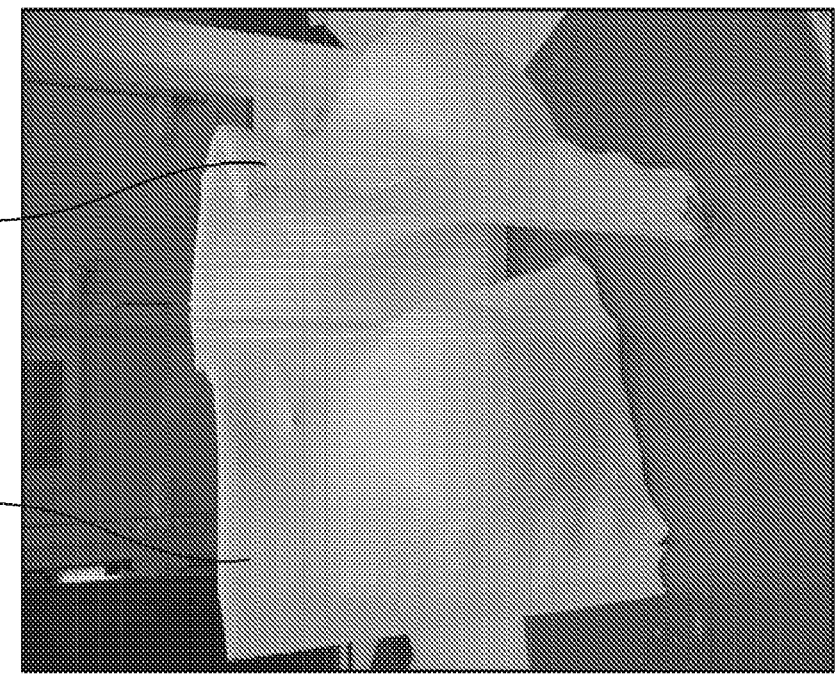
FIGS. 5A-B depict exemplary patient-specific bolus molds according to an embodiment of the disclosure.
Figure 5A:
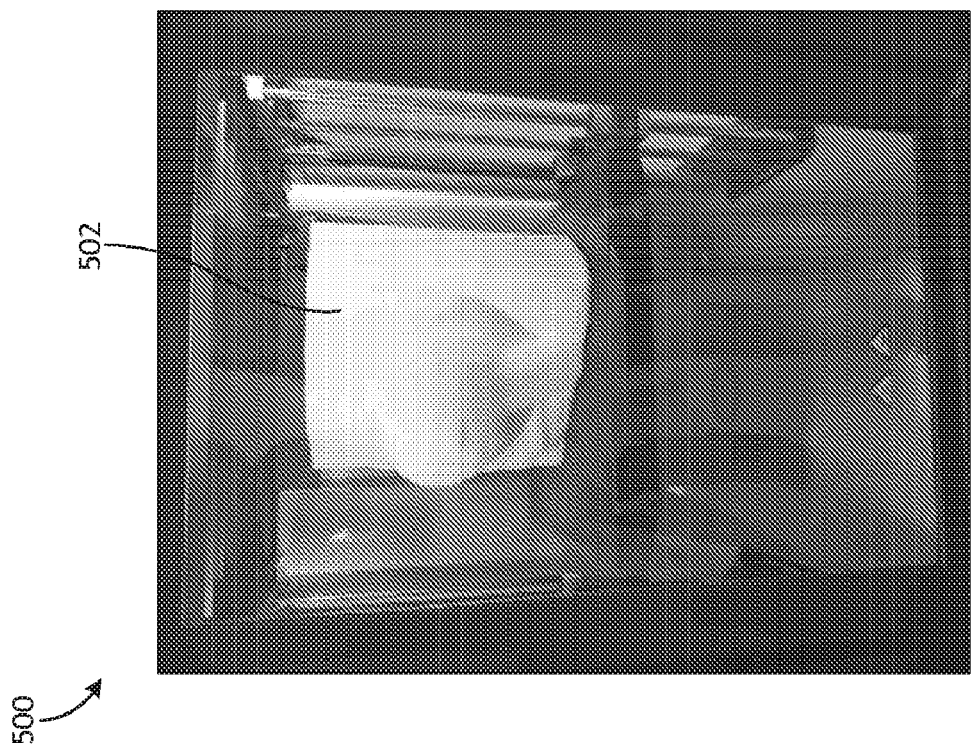

FIGS. 5A-B depict exemplary patient-specific bolus molds 500 according to an embodiment of the disclosure. In FIG. 5A, a 3D printer creates a physical mold 502 of the bolus depicted in the 3D bolus mesh model when the user executes mold generation functionality as described previously. In some embodiments, as shown in FIG. 5B, the physical mold can comprise a positive mold 504 of the bolus and a negative mold 506 of the bolus. The physical mold can then be used to perform the casting steps described previously. In the embodiment shown, by using positive and negative molds to cast the final products, two major challenges brought up by printing the mold directly as one-piece mold are avoided—complexity limitation and roughness surface.

To print more complex bolus, the supporting materials are required for overhanging structures, ridges, bumps, and/or large curvature regions. This applies for almost every layer of fabricating with 3D printing technology. If supporting materials are presented inside the one-piece mold, it is a major challenge to clean up the supporting materials and achieve a clean surface at the same time without breaking up the mold. The mold will end up having a rough surface caused by residue of the supporting materials. This becomes a major limitation for a one-piece mold. Only a simple bolus that has a very gradual surface change could be fabricated by using a one-piece mold. On the contrary, printing positive and negative molds can resolve these issues. Even with the most complex bolus design, the supporting materials could be cleaned up easily with access to all the inner surfaces of the molds. This may reduce a lot of human work during the process of bolus shaping after the moldings are printed. With the embodiments of the interactive interface disclosed herein, one button click can generate a smooth 3D bolus mesh model and mold the model to create both positive and negative molds in .STL files.

FIGS. 6A-B through 9A-B depict various results based on an exemplary experimental implementation of the systems and methods described by an embodiment of the disclosure. First, dosimetric measurements of various bolus materials were gathered. Several square silicone slabs with various thicknesses were made for basic dose measurements such as a PDD profile as well as CT properties. The CT scan was performed on a Philips CT Big Bore system. As a comparison, several other materials such as water, solid water (CNMC Co, Nashville, Tenn.), and a SuperFlab bolus were scanned together with the silicone bolus material. Due to availability of the materials, a 1 cm thick SuperFlab bolus was used. Other materials had at least 5 cm$^3$ dimension. A 0.5 cm$^3$ cube was selected for each material to calculate the mean and standard deviation. The profile and PDD were measured using GaF films (Lot #04051602, Radiation Products Design, Inc.) and 10×10 cm$^2$ field sizes for 3 different energies, 6e, 9e and 6X. Profiles were measured by placing film at depth of 5 cm (6X), 1.7 cm (6e), and 2.6 cm (9e) with 100 cm SAD setting. A 5 mm solid water backscatter slabs were used. PDDs were measured at 100 cm SSD setting. The films were sandwiched between two silicone slabs and aligned with inline crosshair. A total of 6 films were irradiated, each with 300 MU at above 6 settings. Films were scanned with a flatbed scanner (Epson Expression 10000XL) and corrected by recently obtained calibration curve. The results were compared with a treatment planning system (Pinnacle, Philips Healthcare).

End to end tests were conducted on a head phantom (Model 038, Computerized Imaging Reference Systems, Inc. Norfolk, Va.). The bolus generation was simulated in Pinnacle based on old patient cases. Two bolus structures were made for disease sites near 1) the eye and 2) the left ear. Simplified plans were made: 1) AP/PA field at 6X on left ear site, and 2) AP field with 6e and 6 cm open cone on nose site. Optically Stimulated Luminescence Dosimeters (OSLDs) were placed to measure in-vivo doses on the phantom. The OSLDs (nanoDot, Landauer, Glenwood, Ill.) came pre-calibrated and had an accuracy of 5%. Kilo-voltage (kV) images were acquired to determine the actual location of OSLDs on the phantom surface in order to determine the planning doses.

Several patients were treated using the custom silicone bolus. The dose distribution was compared between initial simulation CT with virtual bolus design and rescan CT with the actual bolus. In-vivo doses were measured with OSLDs. Typically, two OSLDs were placed for each patient to get an average result. Locations of the OSLDs were in the middle of the light field or generally at center of crosshair on patient skin. Finally, efficiency on the material cost and time was estimated.

Figure 6A:
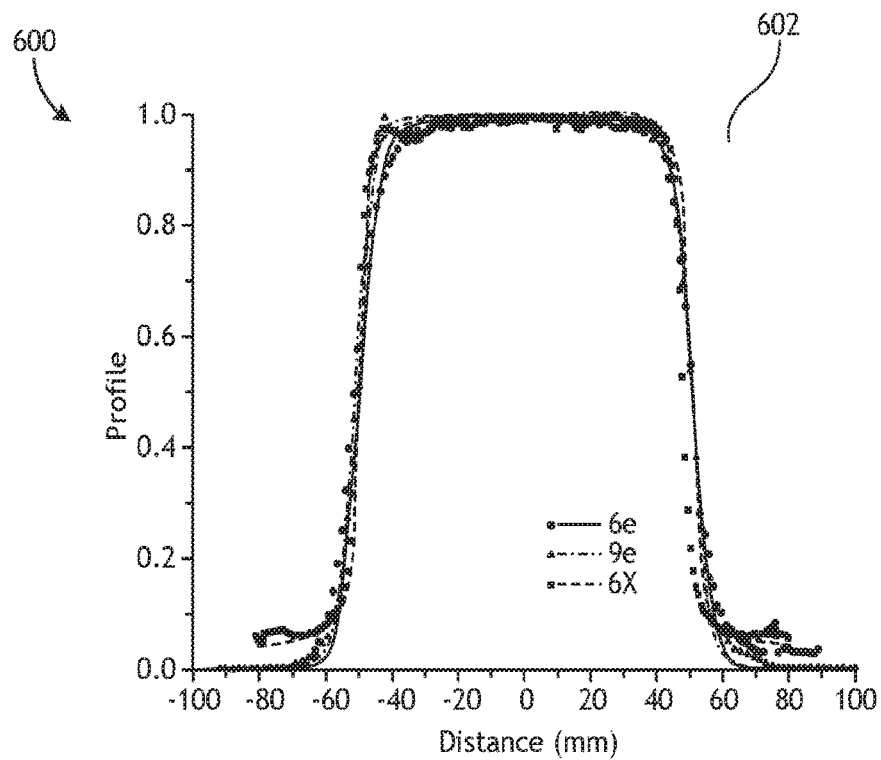
FIGS. 6A-B depict exemplary transverse profiles and percentage depth dose (PDD) comparisons between a silicone bolus and treatment planning system (TPS) properties at multiple energies resulting from an experimental implementation of the systems and methods described by an embodiment of the disclosure.
Figure 6B:
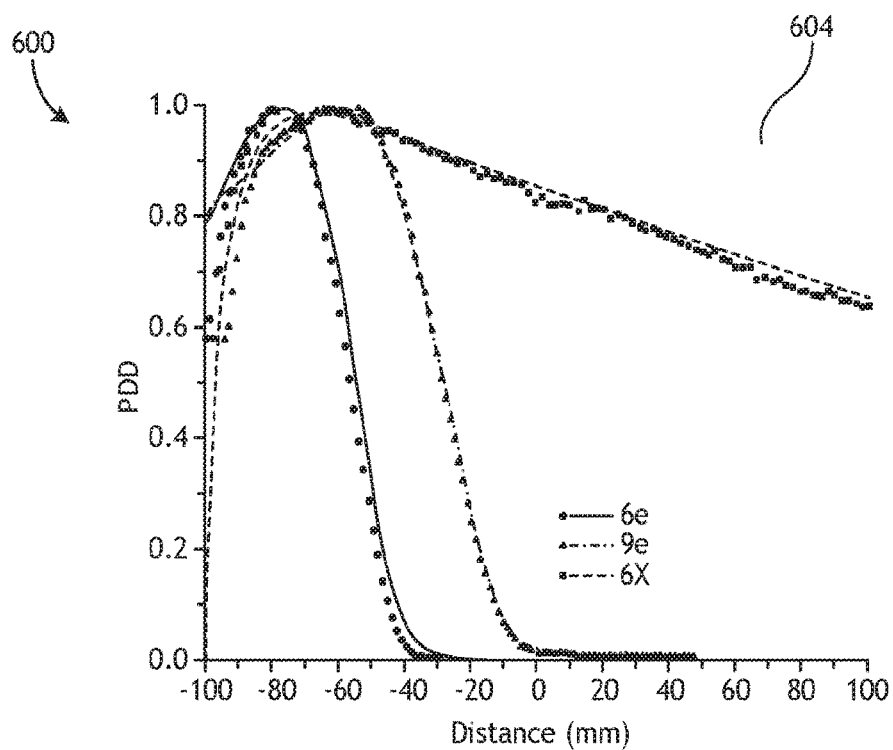

FIGS. 6A-B depict exemplary transverse profiles 602 and percentage depth dose (PDD) 604 comparisons between a silicone bolus and treatment planning system (TPS) properties at multiple energies resulting from an experimental implementation of the systems and methods described by an embodiment of the disclosure.

Listed in Table 1 below is the Hounsfield unit (HU) of various bolus materials together with their physical densities. The CT number generally increases with physical density except for SuperFlab which may be due to a CT partial volume effect from the limited thickness of the material. The standard deviations are small and at a similar level for these materials, indicating good uniformity.

TABLE 1

CT properties of soft bolus material

| Material | CT number | Density(g/cm3) |
|---|---|---|
| Silicone rubber | 139.5 ± 6.4 | 1.07 |
| Water | 3.1 ± 3.3 | 1.00 |
| SuperFlab | −4.7 ± 5.4 | 1.02 |
| Solid water | 11.2 ± 7.3 | 1.04 |

Figures 7A, 7B:
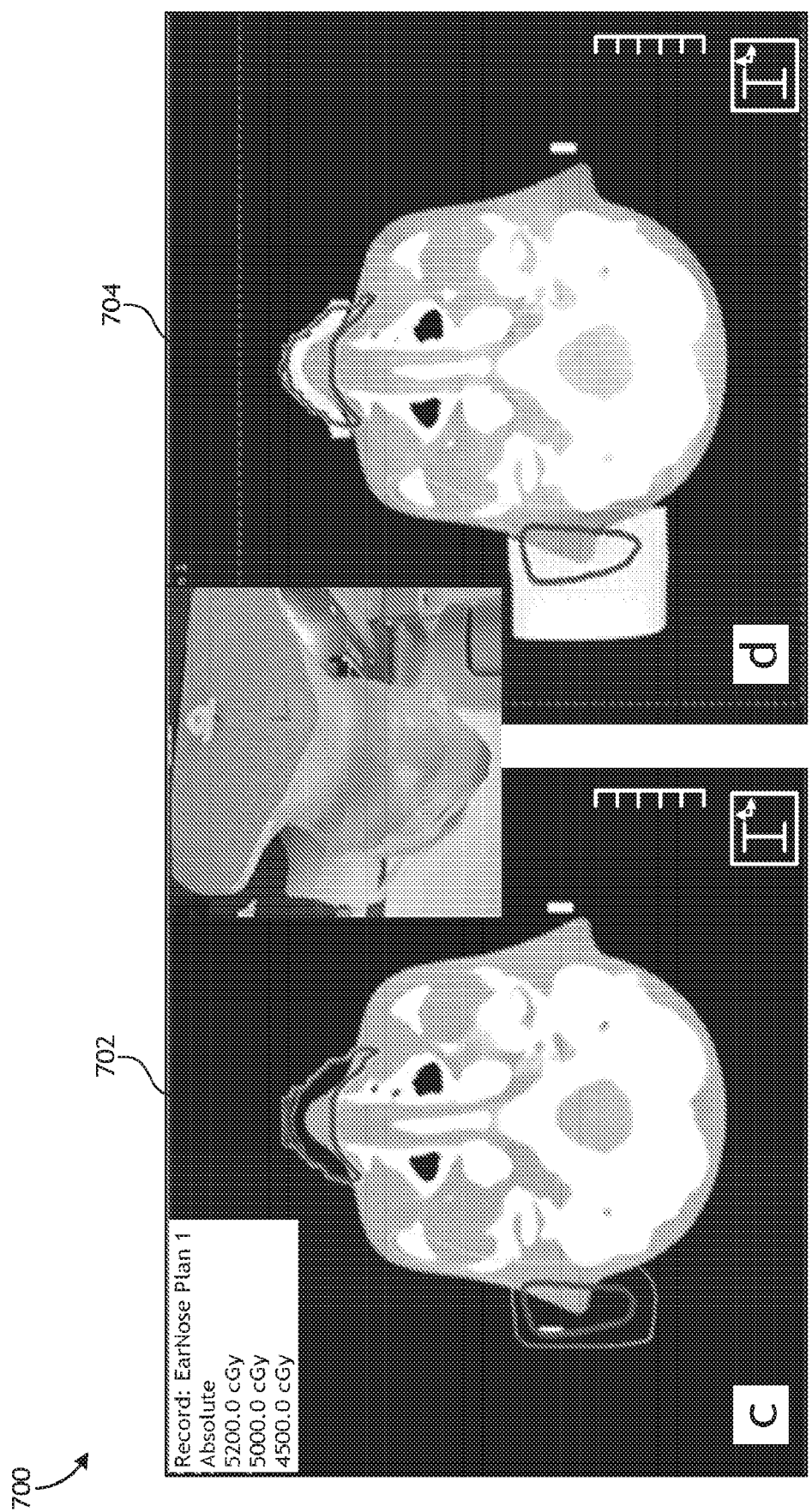
FIGS. 7A-B depict exemplary bolus placements on a head phantom during an experimental implementation of the systems and methods described by an embodiment of the disclosure.
Figure 8:
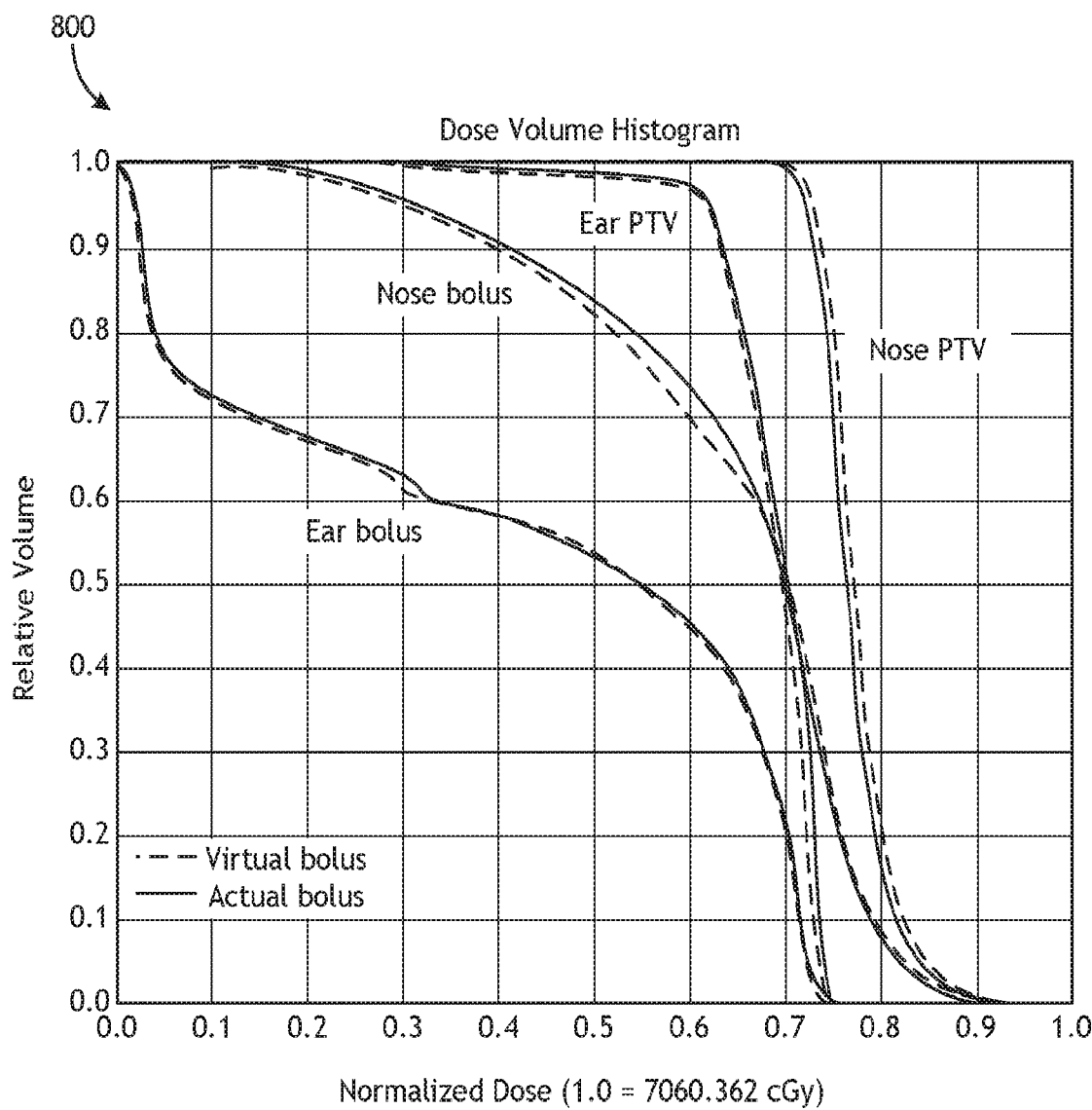
FIG. 8 depicts exemplary dose volume histogram (DVH) curves resulting from an experimental implementation of the systems and methods described by an embodiment of the disclosure.

FIGS. 7A-B depict exemplary bolus placements 700 on a head phantom during an experimental implementation of the systems and methods described by an embodiment of the disclosure. FIGS. 7A-B show the bolus placement on the phantom at rescan. The left ear received 6X AP/PA beams and the nose received 9e beam with 6×6 cm cone. FIG. 7A shows the dose distribution on a virtual bolus plan 702 and FIG. 7B shows the dose distribution on an actual bolus 704 with beams copied from virtual bolus plan. As shown, the bolus fit both regions very well with almost with no gaps. FIG. 8 shows exemplary dose volume histogram (DVH) curves 800 of different structures of the two plans. As shown, the prescription iso-dose lines of FIGS. 7A-B and the DVH curves of FIG. 8 overlap very well between the original virtual plan and the actual boluses.

Figures 9A, 9B:
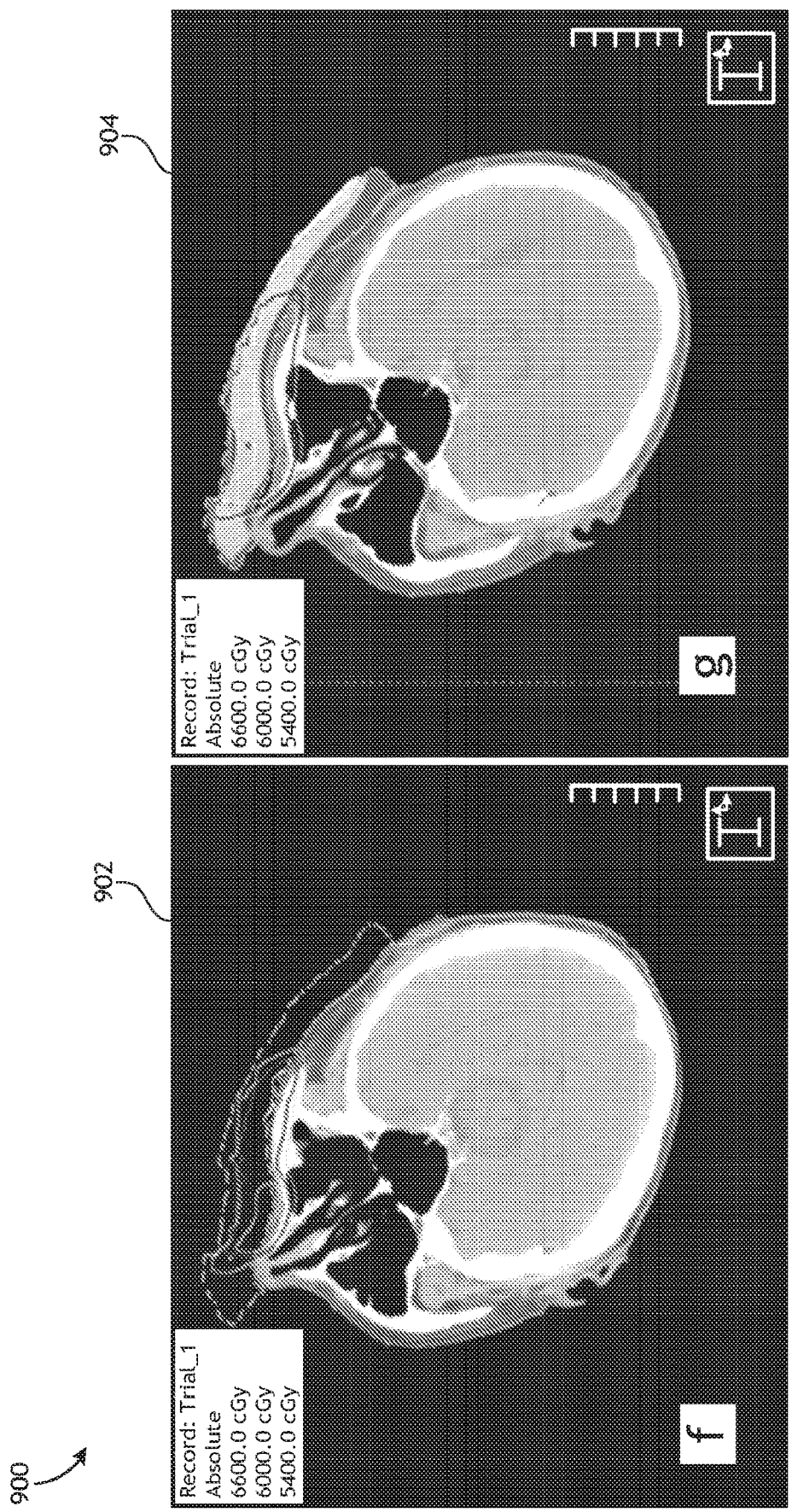
FIGS. 9A-B depict exemplary bolus placements on a real patient during an experimental implementation of the systems and methods described by an embodiment of the disclosure.

FIGS. 9A-B depict exemplary bolus placements on a real patient. FIG. 9A shows dose distributions on a virtual bolus plan 902 and FIG. 9B shows dose distributions on the actual bolus 904 with same beam arrangement and monitor units (Mus) as with the virtual bolus. This shows the plan comparison with a virtual bolus and actual bolus for a patient (e.g., #2, Table 2). This is a patient with shallow lesion at left cheek. The bolus fitted very well with minimal gaps at the bone window display. The prescription iso-dose lines are almost identical between the original plan and the rescan. In-vivo OSLD measurement results were tabulated in Table 2. It was hard to estimate the planned dose due to lack of information on exact OSLD location. Compared with a prescription dose, in-vivo doses were measured within 1-10%.

TABLE 2

In-vivo dose measurements on phantom and information on patient cases

| Patient | Age | Disease | Treatment Site | Bolus volume (cc) | Rx | OSLD reading (cGy) |
|---|---|---|---|---|---|---|
| Phantom | N/A | N/A | nose | 55.8 | 9e, 200cGyx25 to 90% | 190.7 |
| Phantom | N/A | N/A | Lt ear | 166.7 | 6X, 200cGyx25, AP/PA | 199.7 |
| 1 | 70 | skin cancer | Lt Ear | 557 | 6X, 200cGyx25, wedged pair | 198.1 |
| 2 | 77 | head and neck angiosarcoma | Lt cheek | 230 | 9 MeV, 200cGyx 30 to 86% | 220.2 |
| 3 | 68 | Basal cell carcinoma of skin of nose | Nasal cavity | 180 | 18e, 68Gy in 34 fx to 95% | 196.9 |
| 4 | 70 | Basal cell carcinoma of skin | Nose | 499 | 18e, 200cGyx8 to 90% | 189.8 |
| 5 | 68 | subcutaneous, and other soft tissues of head, face and neck | cheek and nose | 98 | 9e, 12e, 300cGyx15 | 302.4 |

The embodiments described herein achieve multiple advantaged over commercially available custom boluses that have been applied in radiation treatment. Because of the nature of hard material, hard boluses inevitably introduces some gaps. They also do not provide for patient comfort especially if the patient has an open wound and they are not easily modified once made. In-vivo measurements with this bolus are not easy because they further generate gaps between the bolus and the skin surface. A 3D printed bolus may be economic and time efficient compared with the commercial hard bolus but it has similar disadvantages of a hard surface even for semi-elastic materials. In addition, a bolus printed by a commercial 3D printer usually prints with 100% fill. This adds a long printing time especially for a large bolus used as a compensator in photon beam radiation. Inhomogeneity associated with an FDM printed bolus may also impact the use in proton therapy and electron therapy.

Compared with hard plastic boluses, soft boluses are skin friendly. Commercially available SuperFlab blouses have been used in radiation therapy clinics for decades. They are reusable and can be used for multiple patients. However, they do not conform well to the patient's skin for regions such as head and neck, scalp, or breast. Other types of bolus materials are not easily shaped to match a desired shape shown in TPS. The custom soft bolus described herein conforms to a patient's skin very well as in-vivo measurements have proved. A summary of cost and effectiveness of different boluses are listed in Table 3. Among them, a soft custom bolus provides the best clinical effectiveness and patient comfort with a reasonable cost.

TABLE 3

Comparison of custom boluses

| Bolus type | Commercial custom bolus | 3D printed bolus (100% fill) | Commercial reusable soft bolus | Soft custom bolus |
|---|---|---|---|---|
| Material cost | *** | ** | * | ** |
| Time cost | *** | ** | none | * |
| Clinical effectiveness | ** | ** | * | *** |
| Patient comfort | ** | ** | *** | *** |

Figure 10B:
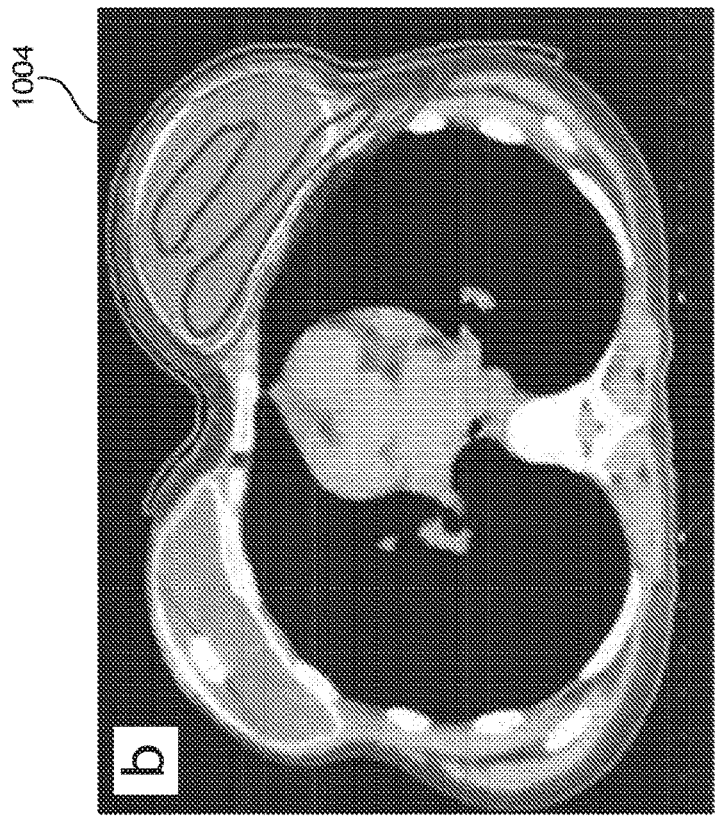
FIGS. 10A-B depict a comparison between a standard hard bolus and an exemplary patient-specific soft bolus created according to an embodiment of the disclosure.
Figure 10A:
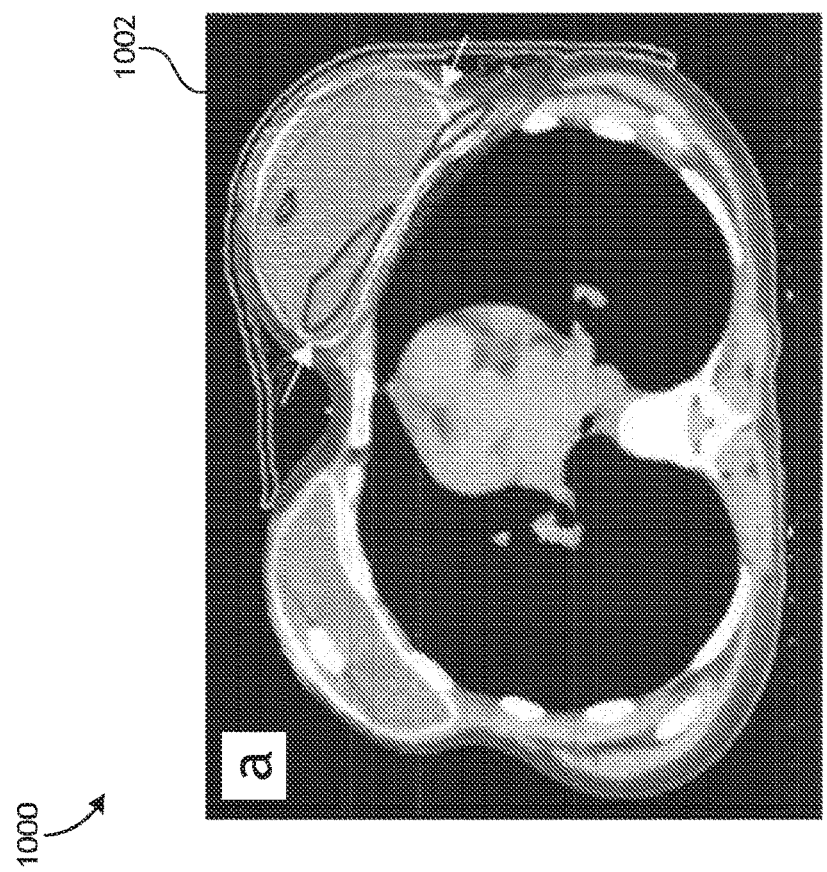

FIGS. 10A-B depict a comparison 1000 between a standard soft SuperFlab bolus 1002 and an exemplary patient-specific soft bolus 1004 created according to an embodiment of the disclosure. As shown in FIG. 10A, the standard soft SuperFlab bolus displays air gaps that cause poor radiation dosimetry in the lateral portion of the breast. As shown in FIG. 10B, a main benefit of the soft custom bolus is that it features no air gaps between the bolus and the patient.

For conventional radiation therapy, the preparation for the treatment under current clinical practice takes about one week from the simulation to the first treatment broken down as follows: Day 1—CT simulation, Day 2 to 4—contouring and planning, Day 3 to 5—quality assurance checks and Day 6 to 8—initial treatment. Depending upon the size and complexity of the desired boluses, the turnaround for manufacturing a silicone bolus using the disclosed embodiments is about 1 to 3 days. Once the bolus structure is ready at Day 2 to 4, the requested boluses could be ready in a quality assurance checking time frame (around Day 3 to 6).

Therefore, the disclosed methods, apparatuses, and systems improve clinical efficiency by using automatic/interactive bolus design interfaces that avoid time-consuming trial-and-error methods; improve dosimetric accuracy for treatment planning by minimizing the air gaps between the bolus and the patient, reducing treatment dose uncertainty and improving radiation coverage; improve dosimetric accuracy for treatment re-planning by providing the ability to rapidly recreate patient-specific boluses during radiotherapy treatment courses as the tumor and/or surface changes; and improve patient comfort because the soft bolus material makes the bolus more comfortable than previously reported 3D bolus concepts that use hard materials.

It may be appreciated that the functions described above may be performed by multiple types of software applications, such as web applications or mobile device applications. If implemented in firmware and/or software, the functions described above may be stored as one or more instructions or code on a non-transitory computer-readable medium. Examples include non-transitory computer-readable media encoded with a data structure and non-transitory computer-readable media encoded with a computer program. Non-transitory computer-readable media includes physical computer storage media. A physical storage medium may be any available medium that can be accessed by a computer. By way of example, and not limitation, such non-transitory computer-readable media can comprise RAM, ROM, EEPROM, CD-ROM or other optical disk storage, magnetic disk storage or other magnetic storage devices, or any other physical medium that can be used to store desired program code in the form of instructions or data structures and that can be accessed by a computer. Disk and disc includes compact discs (CD), laser discs, optical discs, digital versatile discs (DVD), floppy disks and Blu-ray discs. Generally, disks reproduce data magnetically, and discs reproduce data optically. Combinations of the above are also included within the scope of non-transitory computer-readable media. Moreover, the functions described above may be achieved through dedicated devices rather than software, such as a hardware circuit comprising custom very large scale integrated (VLSI) circuits or gate arrays, off-the-shelf semiconductors such as logic chips, transistors, or other discrete components, all of which are non-transitory. Additional examples include programmable hardware devices such as field programmable gate arrays, programmable array logic, programmable logic devices or the like, all of which are non-transitory. Still further examples include application specific integrated circuits (ASIC) or VLSI circuits. In fact, persons of ordinary skill in the art may utilize any number of suitable structures capable of executing logical operations according to the described embodiments.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the disclosed methods, devices, and systems are not intended to be limited to the particular forms disclosed. Rather, they include all modifications and alternatives falling within the scope of the claims, and embodiments other than those shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A system for creating a three-dimensional (3D) representation of a bolus for radiotherapy treatment, the system comprising:

a computer system comprising at least one processor, the computer system configured to:
receive at least one patient-specific radiation treatment planning parameter, where the at least one radiation treatment planning parameter comprises at least one image of a radiotherapy treatment area;
determine a type of beam treatment based on the at least one radiation treatment planning parameter;
create at least one 3D patient-specific bolus model based on the determined type of beam treatment and at least one dosimetric requirement, the at least one 3D patient-specific bolus model comprising a 3D representation of at least one patient-specific bolus for the radiotherapy treatment area;
modify the at least one radiation treatment planning parameter in response to a received input;
based on the modified at least one radiation treatment planning parameter, update the at least one 3D patient-specific bolus model; and
generate data corresponding to the updated at least one 3D patient-specific bolus model, the data configured to enable creation of at least one physical 3D representation of the at least one patient-specific bolus.

2. The system of claim 1, where:
the at least one radiation treatment planning parameter comprises a computed tomography (CT) scan image, a target structure, an avoidance structure, the at least one dosimetric requirement, a radiation beam arrangement, or a combination thereof; and
the at least one dosimetric requirement includes a dosimetric prescription for the target structure, a dosimetric constraint for the avoidance structure, or a combination thereof.

3. The system of claim 1, where the computer system is further configured:
to display at least one radiation dose distribution on the at least one 3D patient-specific bolus model, the at least one radiation dose distribution comprising at least one radiation iso-dose line.

4. The system of claim 3, where the type of beam treatment comprises a photon beam treatment, an electron beam treatment, or a combination thereof.

5. The system of claim 3, where the computer system is further configured to:
receive a first input corresponding to the at least one dosimetric requirement; and
update the at least one 3D patient-specific bolus model based on the first input.

6. The system of claim 5, where the first input comprises an adjustment to the at least one dosimetric requirement.

7. The system of claim 3, where the computer system is further configured to:
receive a second input;
update the at least one radiation dose distribution based on the second input; and
update the at least one 3D patient-specific bolus model based on the updated at least one radiation dose distribution.

8. The system of claim 7, where the second input comprises an adjustment to the at least one radiation iso-dose line of the at least one radiation dose distribution from a first position to a second position.

9. The system of claim 7, where the computer system is further configured to update the at least one 3D patient-specific bolus model in real time based on the updated at least one radiation dose distribution.

10. The system of claim 1, where the computer system is further configured:
to receive a physician dosimetric prescription on a target structure and at least one dosimetric constraint on an avoidance structure.

11. The system of claim 10, where the computer system is configured to:
receive a third input; and
update the physician dosimetric prescription on the target structure and the at least one dosimetric constraint on the avoidance structure based on the third input.

12. The system of claim 11, where:
the received input comprises a first adjustment to the physician dosimetric prescription on the target structure, a second adjustment to the at least one dosimetric constraint on the avoidance structure, or a combination thereof; and
the computer system is further configured to update the at least one 3D patient-specific bolus model in real time based on the updated physician dosimetric prescription on the target structure and the updated at least one dosimetric constraint on the avoidance structure.

13. The system of claim 1, where the computer system is further configured to create a 3D printed mold of the at least one patient-specific bolus, the 3D printed mold comprising a negative shape of the at least one patient-specific bolus.

14. The system of claim 13, where:
the computer system is further configured to initiate a casting process; and
based on initiation of the casting process, a cast based on the 3D printed mold is configured to be produced.

15. The system of claim 1, where the type of beam treatment is determined from a plurality of beam treatments.

16. The system of claim 1, where the received input comprises an adjustment to the at least one patient-specific radiation treatment planning parameter.

17. The system of claim 1, wherein the computer system is further configured to initiate presentation of a graphical user interface, the graphical user interface comprising:
at least one image field that includes at least one image of the radiotherapy treatment area, the at least one 3D patient-specific bolus model, the updated at least one 3D patient-specific bolus model, or a combination thereof;
a patient selection field;
a bolus thickness selection field;
a first selectable option configured to initiate an automatic smoothing operation of the at least one radiation treatment planning parameter; and
a second selectable option configured to enable a manual modification of the at least one radiation treatment planning parameter.

18. A method comprising:
receiving, by a computer system comprising at least one processor, at least one patient-specific radiation treatment planning parameter, where the at least one radiation treatment planning parameter comprises at least one image of a radiotherapy treatment area;
determining, by the computer system, a type of beam treatment based on the at least one radiation treatment planning parameter;
creating, by the computer system, at least one three-dimensional (3D) patient-specific bolus model based on the type of beam treatment determined and at least one dosimetric requirement, the at least one 3D patient-specific bolus model comprising a 3D representation of at least one patient-specific bolus for the radiotherapy treatment area;
modifying, by the computer system, the at least one radiation treatment planning parameter in response to a received input;
based on the modified at least one radiation treatment planning parameter, updating the at least one 3D patient-specific bolus model; and
generating, by the computer system, data corresponding to the updated at least one 3D patient-specific bolus model, the data configured to enable a creation of at least one physical 3D representation of the at least one patient-specific bolus.

19. The method of claim 18, where:
the received input comprises an adjustment to the at least one patient-specific radiation treatment planning parameter;
the at least one radiation treatment planning parameter comprises a computed tomography (CT) scan image, a target structure, an avoidance structure, a radiation beam arrangement, the at least one dosimetric requirement, or a combination thereof; and
the at least one dosimetric requirement includes a dosimetric prescription for the target structure, a dosimetric constraint for the avoidance structure, or a combination thereof.

20. The method of claim 18, further comprising:
displaying, by the computer system, at least one radiation dose distribution on the at least one 3D patient-specific bolus model, the at least one radiation dose distribution comprising at least one radiation iso-dose line.

21. The method of claim 20, where the type of beam treatment comprises a photon beam treatment.

22. The method of claim 20, further comprising:
receiving a first input;
updating the at least one radiation dose distribution based on the first input; and
updating the at least one 3D patient-specific bolus model based on the updated at least one radiation dose distribution.

23. The method of claim 22, where the first input comprises an adjustment to the at least one radiation iso-dose line of the at least one radiation dose distribution from a first position to a second position.

24. The method of claim 23, where the adjustment comprises:
modifying a curvature of the at least one radiation dose distribution; and
modifying a dimension of the at least one radiation dose distribution.

25. The method of claim 22, further comprising updating, by the computer system, the at least one 3D patient-specific bolus model in real time based on the updated at least one radiation dose distribution.

26. The method of claim 18, further comprising:
receiving, by the computer system, a physician dosimetric prescription on a target structure, at least one dosimetric constraint on an avoidance structure, or a combination thereof.

27. The method of claim 26, further comprising:
receiving, at the computer system, a second input; and
updating, based on the second input, the physician dosimetric prescription on the target structure and the at least one dosimetric constraint on the avoidance structure.

28. The method of claim 27, further comprising:
updating, by the computer system, the at least one 3D patient-specific bolus model in real time based on the updated physician dosimetric prescription on the target structure and the updated at least one dosimetric constraint on the avoidance structure; and
where the second input comprises an adjustment to the physician dosimetric prescription on the target structure and the at least one dosimetric constraint on the avoidance structure.

29. The method of claim 18, further comprising creating a 3D printed mold of the at least one patient-specific bolus, the 3D printed mold comprising a negative shape of the at least one patient-specific bolus.

30. The method of claim 29, further comprising casting the at least one patient-specific bolus based on the 3D printed mold.

* * * * *